United States Patent [19]

Short et al.

[11] Patent Number: 4,788,175

[45] Date of Patent: Nov. 29, 1988

[54] CATALYST

[75] Inventors: Glyn D. Short, Yārm; Godfrey C. Chinchen, Spennymoor; James G. Williamson, Stockton-on-Tees, all of England

[73] Assignee: Imperial Chemical Industries PLC, United Kingdom

[21] Appl. No.: 898,400

[22] Filed: Aug. 20, 1986

[30] Foreign Application Priority Data

Aug. 30, 1985 [GB] United Kingdom ................ 8521650

[51] Int. Cl.$^4$ .................... B01J 21/04; B01J 21/10; B01J 23/06; B01J 23/72
[52] U.S. Cl. ................................. 502/342; 518/713
[58] Field of Search ................ 502/307, 342, 343; 518/713

[56] References Cited

U.S. PATENT DOCUMENTS

| | | | |
|---|---|---|---|
| 2,061,470 | 11/1936 | Larson | 518/713 |
| 3,961,037 | 6/1976 | Davies et al. | 502/342 X |
| 4,107,089 | 8/1978 | Bondar et al. | 502/307 |
| 4,279,781 | 7/1981 | Dienes et al. | 502/343 |
| 4,507,403 | 3/1985 | Asakawa | 502/244 X |

FOREIGN PATENT DOCUMENTS

| | | |
|---|---|---|
| 0152648 | 8/1985 | European Pat. Off. |
| 60-122040 | 6/1985 | Japan. |
| 1296212 | 7/1969 | United Kingdom. |
| 1281112 | 7/1969 | United Kingdom. |
| 1159035 | 7/1969 | United Kingdom. |
| 2025418 | 9/1982 | United Kingdom. |
| 2095233 | 9/1982 | United Kingdom. |
| 1405012 | 6/1983 | United Kingdom. |
| 2109262 | 6/1983 | United Kingdom. |
| 2025252 | 6/1985 | United Kingdom. |

*Primary Examiner*—W. J. Shine
*Attorney, Agent, or Firm*—Cushman, Darby & Cushman

[57] ABSTRACT

A catalyst suitable for use in catalytic shift, or methanol synthesis, comprises copper, zinc oxide, magnesia, and at least one trivalent metal oxide, e.g. alumina. The amount of magnesia is such that the magnesium atoms constitute 0.2 to 7% of the total number of copper, zinc, and magnesium atoms.

4 Claims, No Drawings

CATALYST

This invention relates to a catalyst containing metallic copper and an oxidic support material, to a precursor convertible thereto by reduction, to methods of making the catalyst and precursor and to chemical processes catalysed by the catalyst.

A catalyst in common use for the reaction of carbon oxides with hydrogen to synthesise methanol or for the shift reaction of carbon monoxide with steam to give carbon dioxide and hydrogen comprises metallic copper, zinc oxide and at least one further oxide which is usually alumina. Alternative catalysts used in methanol synthesis contain chromia or vanadia in place of alumina. For these reactions there have been many proposals to use copper and zinc oxide only or other further oxides, in place of or in addition to alumina, for example oxides of boron, molybdenum, and rare earth metals and calcium aluminate cement. It has also been proposed to use a copper-silver-zinc oxide catalyst in methanol synthesis and to have iron oxide present in a copper-zinc oxide shift catalyst.

Besides the large-scale uses in methanol synthesis and shift, it has been proposed to use such catalysts in modified methanol synthesis producing dimethyl ether of higher alcohols.

In development work leading to these catalysts the emphasis appears to have lain on the further oxide; thus for example GB-A-1296212 and GB-A-1405012 broadly disclose that other divalent spinel-forming oxides could be used in place of zinc oxide, we find that these are generally inferior. In GB-A-2025252 and GB-A-2025418 there is described a methanol synthesis catalyst containing (when in oxidic precursor form) 20–50% w/w of copper oxide, 15–60% w/w of zinc oxide, 5–3% w/w of alumina or chromium oxide and 0.2–7% w/w of manganese oxides.

We have found that the incorporation of a small proportion of magnesia into copper/zinc oxide/trivalent metal oxide catalysts gives a significant improvement in the stability of the catalysts: i.e. it reduces the rate of decline of activity.

According to the invention a catalyst precursor comprises an intimate mixture of finely divided oxidic materials and containing copper oxide, zince oxide and at least one oxide of a trivalent metal having an ionic radius in the range 0.05 to 0.07 nm, characterised in said mixture also contains magnesia in an amount such that the magnesium atoms constitute 0.2 to 7% of the total number of copper, zince and magnesium atoms in the precursor.

The proportion of magnesia is preferably such that the proportion of magnesium atoms so expressed is over 0.4, and especially in the range 0.6 to 6.0,%. The proportion of copper oxide is typically such that the proportion of copper atoms, expressed in a similar fashion, is at least 20, especially in the range 30 to 75, %. The proportion of zinc oxide is typically such that the proportion of zinc atoms, expressed in a similar fashion, is at least 10, especially in the range 20 to 75, %. The proportion of trivalent metal oxide is typically such that the proportion of trivalent metal atoms is in the range 1 to 50, especially 3 to 30, % of the total number of copper, zinc, magnesium and trivalent metal atoms. It is preferred that at least some of the trivalent metal oxide is present as a highly dispersed or combined form such that it cannot be identified as a distinct single oxide phase by X-ray crystallography. Some of the trivalent metal oxide, or an oxide of another metal, may be present as an identifiable phase in which case it may act as a diluent, or temperature-moderator, or to increase the mechanical strength of the catalyst. Such an oxide, wherein the metal is other than copper, zinc, or magnesium, and that is present as an identifiable phase, may be present to the extent of suitably up to 50% by weight on the total precursor.

The trivalent metal oxide has an ionic radius in the range 0.05 to 0.07 nm. The ionic radius refers to the ions when present in oxides with octahedral coordination and corresponds to their ability to form compound oxides having the spinel structure.

The trivalent oxide is preferably one or more of alumina, vanadia, or chromia. If the intended process use so permits, it can be a more easily reducible oxide, for example iron oxide. (It will be appreciated that "trivalent metal" includes both metals that are solely trivalent and metals capable of forming oxides at other valency levels).

When an identifiable phase oxide is present it is most conveniently alumina. As a further option it can be a difficultly reducible tetravelent oxide, such as titania, zirconia, hafnia, or thoria, or a hydraulic cement such as calcium aluminate.

Other oxides proposed as constituents of methanol synthesis and low temperature shift catalysts, such as rare earth oxides and silver oxide, can be additionally present, if desired.

The catalyst precursor is normally made by wet mixing its components or compounds decomposable thereto. A suitable procedure comprises co-precipitating soluble salts of the metals with a precipitant such as an ammonium, or alkali metal, hydroxide, carbonate, bicarbonate or oxalate. If the trivalent metal forms a salt as an anion, for example, alkali metal aluminates, chromates, or vanadates, such salts can be used. The order in which the reactants are mixed may be optimised following known principles, for example employing single-stage co-precipitation as in GB-A-1159035 or 2-stage co-precipitation as in GB-A-1296212 and GB-A-1405012. Preferably all the divalent oxide constituents are introduced by such co-precipitation. If the catalyst is to be used for dimethylether synthesis or low temperature shift, at least some of the trivalent metal oxide is preferably hydrated, or hydratable, alumina introduced as powdered solid.

After such mixing, the water-soluble material containing the compounds of the metals is washed to remove soluble salts, especially when alkali metal compounds are present, in which event the alkali content should be described to below 0.2, especially below 0.1, % w/w calculated as equivalent $Na_2O$. The washed material is then calcined, for example at 250°–350° C., to convert the metal compounds to oxides. The oxides may then be pelleted, for example by dry-compression, to give a catalyst precursor suitable for use in a fixed bed.

The invention provides further a catalyst corresponding to the precursor but in which copper is present substantially as metallic copper. Usually conversion of precursor to catalyst is effected by the operator of the process to be catalysed, by subjecting the precursor to an activation step in which hydrogen, initially very dilute (for example 0.2% v/v in non-reactive gas such as nitrogen, natural gas, or argon), is passed over the precursor and, as reduction of copper oxide proceeds, the temperature is cautiously increased in the range 100° to 250° C., and the hydrogen concentration also cautiously increased. Analogous procedures using carbon monoxide, or using other diluents, can be employed.

As a further alternative, the precursor can be reduced at an earlier stage, stabilised by contacting with very dilute oxygen at under about 50° C., and marketed in so-called "pre-reduced" condition.

The invention provides processes using the catalyst, in particular:

A. Methanol synthesis in which a gas mixture containing carbon monoxide, and optionally carbon dioxide, and hydrogen is passed over the catalyst at a temperature in the range 200–320° C., a pressure in the range 20–250, especially 30–120, bar abs and a space velocity in the range 500–20000 $h^{-1}$. The process can be on a once-through, or a recycle, basis and can involve cooling by indirect heat exchange surfaces in contact with the reacting gas, or by subdividing the catalyst bed and cooling the gas between the beds by injection of cooler gas or by indirect heat exchange. For this process the catalyst preferably contains copper, zinc oxide and magnesia, with alumina, vanadia, or chromia as the trivalent metal oxide.

B. Modified methanol synthesis in which the catalyst contains also free alumina of surface area 50–300 $m^2 g^{-1}$, or hydrated alumina, so that the synthesis product is relatively rich in dimethyl ether. Temperatures, pressures and space velocities are similar to those for methanol synthesis but the synthesis gas contains hydrogen and carbon monoxide in a molar ratio of less than 2.

C. Modified methanol synthesis in which the catalyst contains also alkali, so that the synthesis product contains higher alcohols (containing 2 to 5 carbon atoms), usually in addition to methanol. Process conditions are generally similar to those for B, but higher pressures and temperatures and lower space velocities in the stated ranges are preferred.

D. Low temperature shift reaction in which a gas containing carbon monoxide (preferably under 4% v/v on a dry basis) and steam (steam to total dry gas molar ratio typically in range 0.3 to 1.5) is passed over the catalyst in an adiabatic fixed bed at an outlet temperature in the range 200°–300° C. Usually the inlet gas is the product of "high temperature shift" in which the carbon monoxide content has been decreased by reaction over an iron-chromia catalyst at an outlet temperature in the range 400°–500° C., followed by cooling by indirect heat exchange. The outlet carbon monoxide content is typically in the range 0.1 to 1.0%, especially under 0.5% v/v on a dry basis.

E. Medium temperature shift in which the gas containing carbon monoxide and steam is fed to the catalyst at an inlet temperature in the range 250°–325° C. and the outlet temperature is up to 400° C. These conditions are more severe than in D, such that the new catalyst is expected to be especially advantageous.

F. Low-medium temperature shift with heat exchange, in which the reaction in the catalyst bed occurs in contact with heat exchange surfaces. The coolant on the cold side of such surfaces can be, for example, gas or a diphenyl-ether-diphenyl or like heat transfer liquid. More conveniently it is water under such a pressure such that partial, or complete, boiling takes place. A suitable pressure is 15 to 50 bar abs and the resulting steam can be used, for example, to drive a turbine or to provide process steam for shift, or for an upstream stage in which the shift feed gas is generated. The water can be in tubes surrounded by catalyst or vice versa.

Two particular modes of operating this type of shift process are envisaged:

(i) Falling temperature profile, for example 240°–350° C. inlet range and (especially 240°–310° C.) with typically a fall of up to 50° C. (especially 10°–30° C.) between inlet and outlet. This permits better heat recovery upstream because a feed gas produced at high temperature can be cooled to a temperature lower than in the conventional process in which the high temperature shift step requires an inlet temperature of 370°–400° C. It also permits an outlet carbon monoxide content as low as in conventional low temperature shift;

(ii) Rising temperature profile, for example at an inlet temperature in the range 100°–240° C. rising to a maximum of 240° to 350° C., followed by a falling temperature profile as in (i) above. This is suitable for shifting a gas made by partial oxidation of coal, or heavy hydrocarbon feedstocks, followed by treatments at ambient temperature, or below, to remove carbon, dust and sulphur compounds. The hot water in heat exchange brings the feed gas up to the temperature at which the shift reaction proceeds rapidly. In such a process the inlet zone in the shift catalyst bed may be a preheat zone charged with inert granules such as alpha alumina.

In any such shift processes it is desirable to protect the catalyst from poisoning, such as by sulphur or chlorine compounds, and for this purpose a guard bed of expendible catalyst or zinc oxide or alkalised alumina can be disposed upstream.

Processes involving heat exchange are described further in EP-A-157480. The provision of the heat exchange also assists in controlling catalyst temperature during reductive activation and also, by coping with any fall in temperature below the dewpoint of steam, makes it practicable to use a chloride guard, such as alkalised alumina, in an inlet zone above the catalyst.

The invention is illustrated by the following examples.

EXAMPLE 1

Methanol synthesis

Catalyst precursor preparation

A series of catalyst precursors A–G was made by (a) co-precipitating the nitrates of copper, zinc, aluminium, and magnesium with sodium carbonate at 70° C. with slight alkalinity at the end of reaction;

(b) washing the precipitate by decantation until its alkali content was 0.1% w/w calculated as $Na_2O$ on the non-volatiles present;

(c) collecting the precipitate on a filter, drying it at 120° C. overnight and calcining it at 300° C. for 6 hours; and (d) crushing the resulting oxide mixture to a fine powder, mixing it with 3% w/w of graphite powder and compressing it into 3.6×5.4 mm squat cylindrical pellets.

Two catalyst precursors H, I were made by a similar procedure, but using manganese nitrate instead of magnesium nitrate.

For a control a sample J of magnesia-free catalyst prepared commercially by a scaled-up version of the same procedure was provided.

Catalyst precursors A–G were shown by analytical electron microscopy to consist mainly of a CuO—ZnO—MgO—$Al_2O_3$ and a ZnO—$Al_2O_3$ phase substantially free of GuO and MgO, with substantially no free MgO or $Al_2O_3$.

Catalyst test (a) Methanol synthesis (small scale)

A sample of the pellets was ground and 2 ml of fragments in the sieve range 18 to 25 BSS were charged to a micro-reactor and reduced to active catalyst in a 2% v/v $H_2$ in $N_2$ at up to 210° C. A methanol synthesis gas of % v/v composition 10 CO, 3 $CO_2$, 67 $H_2$, 20 $N_2$ was passed over the catalyst at a pressure of 50 bar abs, temperature 250° C. and space velocity 40000 $h^{-1}$. The outlet methanol percentages was measured. Then, for an accelerated life test, the pressure was raised to 100 bar abs and the temperature to 300° C.; these conditions were held for 168 h, then decreased to their former levels, at which the outlet methanol content was measured again.

The composition and activity of the catalysts tested, and the die-off rate assessed by the loss in activity due to the high temperature run, are shown in Table 1. The activity quoted is relative to that of the standard, catalyst J. The die-off rate is defined as the ratio of the difference between the initial and final activities of the sample to the difference between the initial and final activities of the standard, catalyst J.

TABLE 1

| Catalyst | composition % metal atoms | | | | | R* (%) | Activity (fresh) | Die off rate |
|---|---|---|---|---|---|---|---|---|
| | Cu | Zn | Al | Mg | Mn | | | |
| A | 53.7 | 26.8 | 18.6 | 0.9 | 0 | 1.1 | 0.94 | 0.35 |
| B | 58.1 | 24.4 | 15.4 | 2.0 | 0 | 2.4 | 0.95 | 0.29 |
| C | 59.0 | 23.5 | 15.1 | 2.4 | 0 | 2.8 | 1.11 | 0.53 |
| D | 56.4 | 24.1 | 16.5 | 3.0 | 0 | 3.6 | 1.00 | 0.27 |
| E | 56.0 | 21.4 | 19.2 | 3.4 | 0 | 4.3 | 0.98 | 0.49 |
| F+ | 58.6 | 19.8 | 15.6 | 6.0 | 0 | 7.1 | 1.02 | 0.85 |
| G+ | 55.2 | 20.3 | 18.4 | 6.1 | 0 | 7.5 | 1.05 | 1.20 |
| H+ | 51.1 | 22.6 | 17.3 | 0 | 8.9 | 10.8 | 0.97 | 1.34 |
| I+ | 56.1 | 25.1 | 15.3 | 0 | 3.5 | 4.1 | 0.80 | 1.0 |
| J+ | 55.6 | 27.1 | 17.3 | 0 | 0 | 0 | 1.0 | 1.0 |

*R is defined as the ratio of the number of magnesium (or manganese) atoms to the total number of magnesium (or manganese), copper, and zinc atoms in the catalyst.
+comparative It is evident that by part replacement of zinc by a small amount of magnesium, a slower activity loss can be obtained. However, manganese does not provide the same useful effect.

(b) Methanol synthesis (pilot plant)

A batch, prepared on a larger scale, of a pelleted catalyst precursor of composition similar to that of precursor E but containing 2.0% by metal atoms of Mg was activated and tested in a side-stream unit operated in parallel with an industrial methanol synthesis plant. The inlet gas composition was subject to variation owing to varying plant duty requirements but was typically (% v/v) 10 $CO_2$, 6 CO, 66 $H_2$, 16 $CH_4$, 2 $N_2$, the pressure was 100 bar abs. and the space velocity about 12500 $h^{-1}$. The extent of methanol formation was determined by measuring the catalyst outlet temperature. A commercial methanol synthesis catalyst was tested as a standard at the same time in a parallel small reactor. Table 2 shows the inlet and outlet temperatures over a period of 75 days.

TABLE 2

| Day No. | Temperature °C. | | |
|---|---|---|---|
| | Inlet | Outlet (invention) | Outlet (standard) |
| 2 | 225 | 290 | 290 |
| 11 | 230 | 287 | 284 |
| 24 | 238 | 290 | 286 |
| 30 | 233 | 290 | 255 |
| 36 | 230 | 285 | 254 |
| 50 | 234 | 287 | 272 |
| 53 | 240 | 292 | 278 |
| 60 | 235 | 284 | 259 |
| 70 | 236 | 290 | 252 |
| 75 | 238 | 290 | 250 |

It is evident that at 75 days the temperature-rise and thus the rate of methanol synthesis is substantially the same as at 2 days when using the invention catalyst, but has decreased by about 75% when using the commercial catalyst.

(c) Low temperature shift

An 18 ml sample of the batch of oxide precursor used in (b) was charged to a laboratory reactor and reduced to active catalyst by passing over it a dilute hydrogen-nitrogen mixture and increasing the hydrogen concentration and temperature slowly; the temperature was not allowed to exceed 250° C. Then a shift feed mixture as follows (% v/v)

CO: 5.7
$CO_2$: 7.14
$N_2$: 22.86
$H_2$: 35.7
$H_2O$: 28.6 was passed over it at 36 bar abs pressure, space velocity 70000 $h^{-1}$, outlet temperature controlled in the range 256°–294° C., for 314 hours. The outlet gas was at intervals analysed for CO; percentage conversions, are set out in Table 3 in comparison with those obtained using a commercially available copper-zinc oxide-alumina low temperature shift catalyst as a standard.

TABLE 3

| Time, (h.) | Invention | | Standard | |
|---|---|---|---|---|
| | Temp (°C.) | (%) | Temp (°C.) | (%) |
| 50 | 294 | 88 | 283 | 61 |
| 74 | 291 | 82 | 281 | 58.5 |
| 122 | 268 | 84 | 279 | 57 |
| 146 | 256 | 84 | 285 | 58 |
| 206 | 293 | 84 | 279 | 53 |
| 230 | 286 | 87 | 277 | 52 |
| 314 | 269 | 83.5 | 276 | 47 |

It is evident that the invention catalyst is more active and stable than the commercial catalyst standard.

What is claimed is:

1. A catalyst precursor comprising an intimate mixture of finely divided oxidic materials and consisting essentially of copper oxide, zinc oxide, alumina, and magnesia, the proportion of magnesia being such that the magnesium atoms constitute 1.1 to 7% of the total number of copper, zinc and magnesium atoms in the precursor, and the proportion of alumina being such that the aluminum atoms constitute 3 to 30% of the total number of copper, zinc, aluminum, and magnesium atoms in the precursor.

2. A catalyst precursor according to claim 1 wherein the proportions of copper and zinc oxides are such that the copper atoms constitute at least 20%, and the zinc atoms constitute at least 10%, of the total number of copper, zinc, and magnesium atoms in the precursor.

3. A catalyst precursor according to claim 2 wherein the proportions of copper, magnesium, and zinc oxides are such that the copper atoms constitute 30 to 75%, the magnesium atoms constitute 1.1 to 6%, and the zinc atoms constitute 20 to 75%, of the total number of copper, zinc, and magnesium atoms in the precursor.

4. A catalyst corresponding to a precursor according to claim 1 but in which the copper oxide has been reduced substantially to metallic copper.

* * * * *